United States Patent [19]
Crosby et al.

[11] Patent Number: 5,693,000
[45] Date of Patent: Dec. 2, 1997

[54] CARDIOMYOPLASTY SIMULATOR WITH FEEDBACK CONTROL

[75] Inventors: Peter A. Crosby, Englewood; Stuart B. McConchie, Parker, both of Colo.; Gordon Jacobs, Norristown, Pa.; Tuan Bui, Highlands Ranch, Colo.

[73] Assignee: Pacesetter, Inc., Sylmar, Calif.

[21] Appl. No.: 659,580

[22] Filed: Jun. 6, 1996

[51] Int. Cl.⁶ .................................................. A61M 1/00
[52] U.S. Cl. ................................................................. 600/16
[58] Field of Search .......................... 600/16, 17; 607/9

[56] References Cited

U.S. PATENT DOCUMENTS

| | | | |
|---|---|---|---|
| 5,067,960 | 11/1991 | Grandjean | 623/3 |
| 5,098,442 | 3/1992 | Grandjean | 623/3 |
| 5,251,621 | 10/1993 | Collins | 607/4 |
| 5,358,519 | 10/1994 | Grandjean | 600/16 |

*Primary Examiner*—Scott Getzow
*Attorney, Agent, or Firm*—Gottlieb, Rackman & Reisman

[57] ABSTRACT

A cardiomyoplastic muscle is stimulated electronically using a closed loop control system. As part of the system, a signal sensed the muscle which is characteristic of its condition. If this signal indicates an abnormal condition, then the stimulation of the muscle is modified accordingly.

23 Claims, 3 Drawing Sheets

5,693,000

CARDIOMYOPLASTY SIMULATOR WITH FEEDBACK CONTROL

BACKGROUND OF THE INVENTION

A. Field of Invention

This invention pertains to an implantable cardiac device including a muscle arranged and constructed to assist a patient's heart, and more particularly to a device which monitors the status of the muscle and controls its stimulation accordingly.

B. Description of the Prior Art

Cardiomyoplasty is a procedure for treating mechanical failure of the heart, as a result of cardiac disease such as dilated cardiomyopathy. In this procedure, the large skeletal muscle of the back, is dissected away from where it joins the spine, is inserted through an aperture made in the ribs, and wrapped around the heart muscle. A cardiomyoplasty stimulator electrically stimulates the latissimus dorsi muscle via a pair of fine wire electrodes threaded through the muscle. The muscle stimulations are timed to coincide with normal cardiac contractions, as determined from signals sensed via a conventional heart pacemaker lead system, either endocardially or epimyocardially.

One of the fundamental problems with the cardiomyopiasty procedure is that the force of contraction of the latissimus dorsi is unregulated. This may lead to insufficient force being generated, or conversely more force being generated than is needed. A collateral problem is that the skeletal muscle can fatigue, leading to its gradual degradation and loss of function. However, tiring the muscle may be avoided if the muscle is not delivering more force (work or power) than actually necessary. Therefore it would be advantageous to measure the force generated by the muscle during each contraction, and to determine the beginning of fatigue state of the muscle, and use this information to regulate the strength of contraction, or the ratio of augmented cardiac cycles to unaugmented cycles, to allow the skeletal muscle time to rest and recover.

Previous inventions by Grandjean (see U.S. Pat. Nos. 5,098,442 and 5,067,960) have disclosed the use of intramuscular pressure or colorimetry to measure oxygen concentration in the muscle blood supply to determine fatigue in the muscle. While these systems may or may not work, they require a special lead with a sensor inserted into the skeletal muscle, with attendant problems of reliability and cost.

It is well known from the work associated with electromyographic signals obtained from skeletal muscles that the characteristics of these signals change with the onset of fatigue, and can be determined by straight forward signal processing (see Basano, L., & Ottonello, P., "Real Time FFT to Monitor Muscle Fatigue", IEEE Trans on Biomed Eng. BME-33:1049-1051 1986, and Park, E, & Meek, S. G., "Fatigue Compensation of the Electromyographic Signal for Prosthetic Control and Force Estimation", EEEE Trans on Biomedical Engineering, 40: 10 Oct. 1993). It appears that the most reliable predictor of the onset of fatigue in skeletal muscle based on the EMG is a change in the frequency spectrum (see Beliveau, L., van Hoecke, J., Garapon-Bar, C., Gaillard, E., Herry, J. P., & Bouissou, A. P., "Myoelectrical and Metabolic Changes in Muscle Fatigue", Int. J. Sports Med 13(1992) S 153–S 155).

The relationship between muscle force and electromyogram for a latissimus dorsi muscle used for cardiac assistance was investigated by Cestari et al (Cestari, I. A., Moreira, L. F. P., Hayashida, S. A., Leimer, A. A., & Jatene, A. D., "Alternative Parameters for Evaluating the Performance of Skeletal Muscle in Cardiac Assistance", J. Cardiac Surg., 6:1 Supplement, 1991), and promising results were shown, but no modified myostimulation device or method of measurement was disclosed in this reference.

OBJECTIVES AND SUMMARY OF THE PRESENT INVENTION

In view of the above-mentioned disadvantages of the prior art, it is an objective of the present invention to provide an implantable cardiac device having means for reliably monitoring the status of a muscle used for cardiomyoplasty.

A further objective is to provide a cardiac device with a closed loop feedback system wherein the stimulation of the muscle is controlled based on its condition.

Yet another objective is to provide a cardiac device which automatically adjusts its operation as the muscle is trained.

A further objective is to provide an apparatus and method whereby the electrical signal produced by the muscle responsive to stimulation and contraction is used as a control parameter in a closed loop control system.

Other objectives and advantages of the invention shall become apparent form the following description.

Briefly, an implantable cardiac device constructed in accordance with this invention includes two components: an electrical component consisting of a hermetic housing containing electronic control circuitry and a biological muscle wrapped around a heart, another organ of the cardiovascular system of a patient or otherwise arranged to provide cardiac assistance. The electronic component is coupled to the heart and to the muscle by electrodes for collecting information and for providing stimulation pulses thereto. The electronic component includes means for monitoring the condition of the muscle and means for adjusting the muscle stimulation parameters in accordance with the muscle condition. The means for monitoring the muscle may include means for sensing an intrinsic electrical characteristic the muscle, such as electromyogram signals, impedance measuring means for measuring an impedance of muscle related to its condition, or frequency analyzing means for analyzing the frequency of the signals in the muscle. The signals obtained from the muscle are compared to stored signals representative of the condition of the muscle based on data previously obtained from the muscle, or data developed from statistical analysis of muscles from other patients. The result of the comparison is then used to adjust (if necessary) the stimulation of the muscle and the heart.

DETAILED DESCRIPTION OF THE PREFERRED EMBODIMENT

Figure 1:
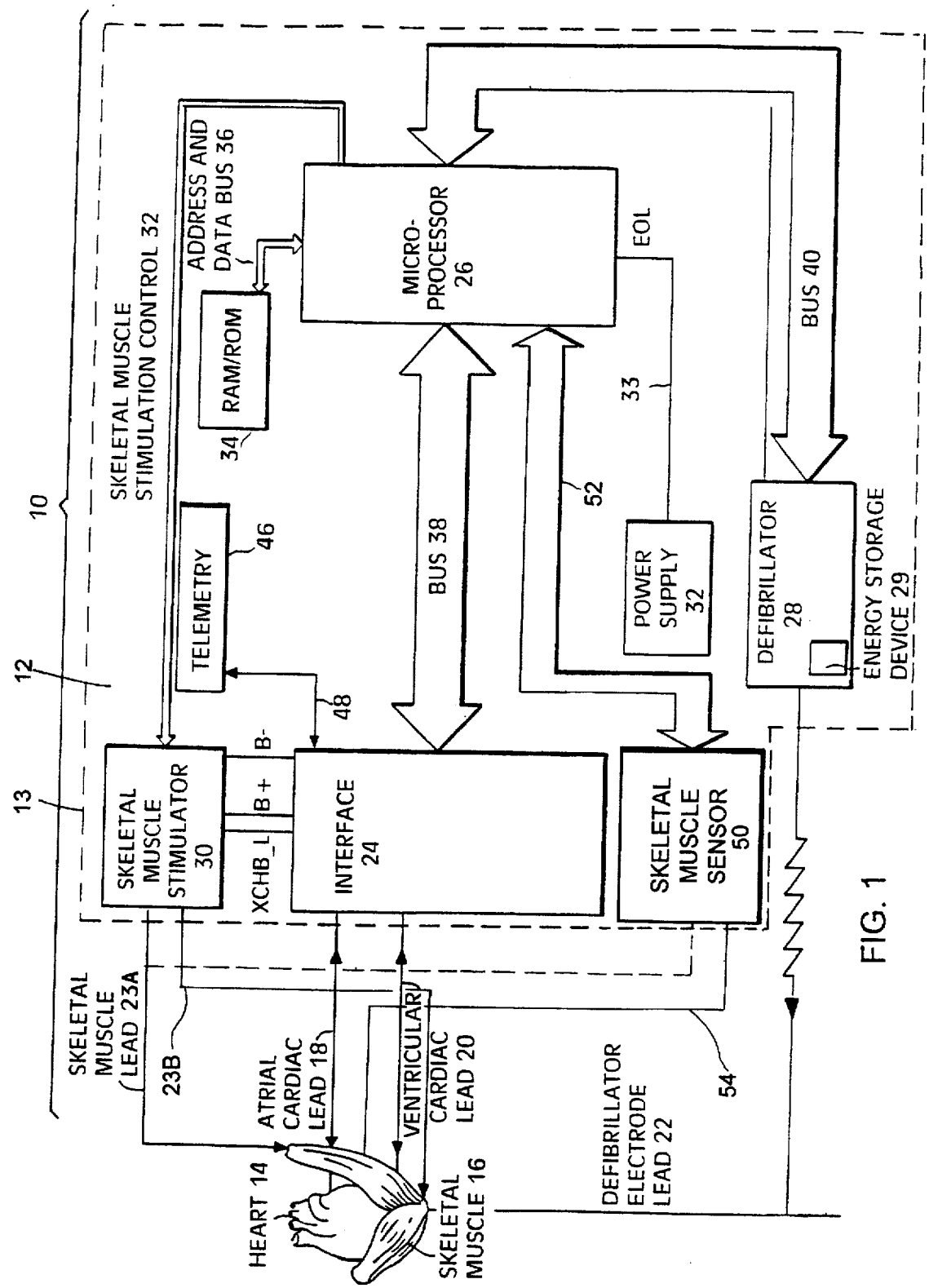
FIG. 1 shows a block diagram of an implantable cardiac device constructed in a accordance with this invention.

In FIG. 1 there is depicted a block diagram of an implantable cardiac device 10. The device 10 is designed to be implanted within a patient and includes a hermetically sealed electronic module 12 having a hermetically sealed housing 13. The device 10 further includes a muscle 16 wrapped about the heart 14. It should be understood that the muscle may also be positioned about another organ of the cardiovascular system as well.

Leads are also provided for connecting module 12 to a patient's heart 14 and skeletal muscle 16. These leads may include an atrial cardiac lead 18, a ventricular cardiac lead 20 extending to the atrium and the ventricle of the patient's heart 14, respectively, as well as a defibrillation electrode lead 22 and a pair of skeletal muscle lead 23A, 23B.

The pulse module 12 generally includes an analog/digital interface 24, a microprocessor 26, a defibrillator 28, a skeletal muscle stimulator 30 and a power supply 32. The interface 24 is provided for the detection of analog signals representing cardiac electrical activity and for the delivery of pacing pulses to the heart over leads 18 and 20. The microprocessor 26, in response to various inputs received from the interface 24 as well as from a defibrillator 16, performs various operations so as to generate different control and data outputs to module interface 24, skeletal muscle stimulator 30 and defibrillator 28. The power supply 32 provides reliable voltage to the other components of the pulse module. When the power supply 32 is nearly exhausted it generates an End-Of-Life (EOL) signal on line 33 to the microprocessor 26.

Skeletal muscle stimulator 30 generates electrical pulses on a skeletal muscle leads 23A, 23B for stimulating the skeletal muscle 16. Details of the manner in which the skeletal muscle stimulator operates can be found in U.S. Pat. No. 5,251,621 incorporated herein by reference.

The defibrillator 28 has an energy storage device 29 which may consist of one or more capacitors (not shown), and is used to produce high voltage pulses responsive to control signals from microprocessor 26 received on bus 40. The defibrillator electrode lead 22 transmits the defibrillator shocks from the implanted module 12 to the heart 14.

The microprocessor 26 is connected to a Random Access/Read Only memory unit 34 by an address and data bus 36. Unit 34 is used to store data and programming for microprocessor 26.

The module 12 also includes a telemetry circuit 46 over which control and data signals can be exchanged with the outside world. The telemetry circuit 46 is coupled to interface 24 by a bus 48.

As more fully described below, microprocessor 26 and interface 24 are connected by a data and communication bus 38 for exchanging various data.

The skeletal muscle stimulator 30 shown in FIG. 1, receives input signals from microprocessor 26 over the skeletal muscle stimulation control bus 32. In addition, the interface 24 supplies to stimulator 30 battery power over two battery leads B+ and B− which provide energy for biphasic skeletal muscle stimulation. The battery leads B+, B− are floating with respect to the power supplied by supply 32 to provide signal isolation. Interface 24 receives a signal XCHB_L, which is a cross channel blanking control signal used to disable cardiac sensing by the interface 24 during generation of a skeletal muscle stimulation pulse. Therefore this signal prevents the microprocessor 26 from incorrectly classifying a skeletal muscle stimulation pulse as an episode of intrinsic cardiac activity. Details of the skeletal muscle stimulator are provided in commonly assigned U.S. Pat. No. 5,251,621, incorporated herein by reference.

Details of the interface 24 and its method of operation are found in U.S. Pat. No. 5,251,621 discussed above and incorporated herein by reference.

Importantly, module 12 further includes a skeletal muscle sensor 50. The sensor 50 is connected to microprocessor 16 by a bus 52, and to muscle 16, in one embodiment by an electrode 54. The purpose of the sensor 50 is to determine the condition of the muscle 16, i.e., whether the muscle 16 is still not fully trained and needs further training, or the muscle is over- or under excited, or the muscle is tired. The muscle condition information is sent to the microprocessor via bus 52, which in response modifies its commands to the muscle stimulator 30, and, if required, to interface 24.

Figure 2:
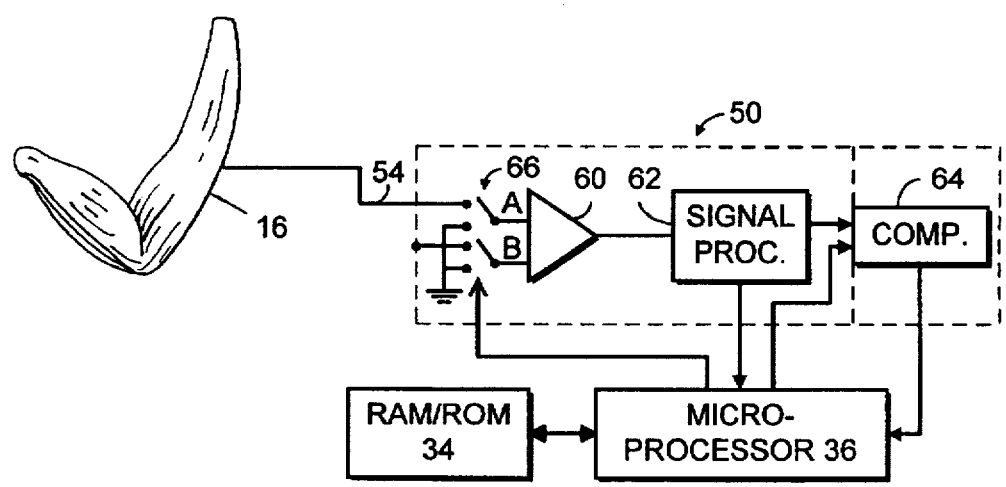
FIG. 2 shows a first muscle sensor for the cardiac device of FIG 1.

Details of one embodiment of the invention are shown in FIG. 2. In this embodiment the sensor 50 includes an amplifier 60, a signal processor 62 and a waveshape comparator 64. The amplifier 60 has one input A connected via a DPDT switch 66 to electrode 54. The other input B of the amplifier 60 is connected through switch 66 to the housing 13 of module 12. The housing is metallic so that it provides a large ground return electrode. The amplifier 60 thus selectively monitors activity of the muscle 16 through the electrode 54. The distal end of electrode 54 is positioned either adjacent to, in between, or a distance away from the electrodes 23A, 23B.

During stimulation of muscle 16, switch 66 is used to ground inputs A and B to protect amplifier 60 from saturation. In between stimulations, the switch 66 is used to enable the amplifier to sense an intrinsic EMG waveform generated with muscle 16. This waveform is analyzed and conditioned by signal processor 62 and then fed to a comparator 64. Comparator 64 also receives as an input information from microprocessor 36 based on data from memory 34 defining a waveform characteristic of one or more preselected muscle conditions. For example, memory 34 may have information describing waveforms characteristic of muscles in various conditions (i.e., trained, untrained, tired, rested, underexcited, over-excited, etc.) By comparing the signals from processor 62 with the signals from the microprocessor 36, sensor 50 can thus determine substantially instantaneously the condition of muscle 16.

Figure 5:
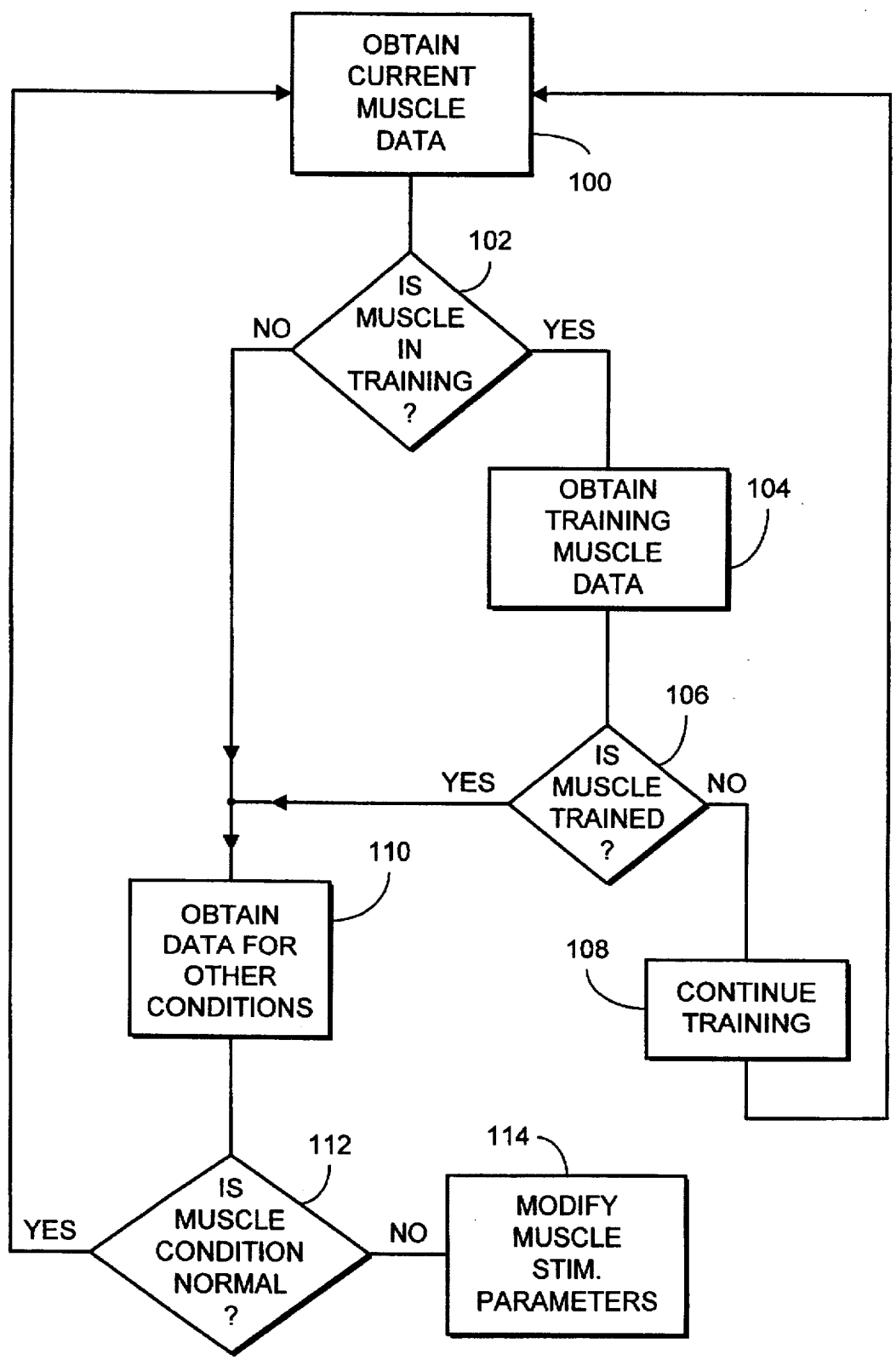
FIG. 5 shows a flow chart for the operation of the cardiac device of FIGS. 1–4.

Referring to the flow chart of FIG. 5, in step 100 current muscle data is obtained. In step 102 a test is performed as to whether the muscle is still in training. If the training period has not expired, then in step 104 data is obtained from memory 34 descriptive of trained muscles. In step 106 the EMG is compared to data from the memory characteristic of trained muscles. If the data match, indicative that the muscle is now trained than the steps of FIG. 5B is performed. If no match is found than in step 108 a decision is made to continue training and the next EMG is obtained (step 100). Training may be continued for a predetermined time period or until it is determined that the muscle has been trained in step 106.

If it is determined that the training period has expired (step 102), or that the muscle has been trained (step 106), then in step 110 data is obtained from memory corresponding to other muscle conditions, i.e., over-stimulated, under-stimulated, etc.

In step 112 the current muscle condition data is compared sequentially with data from memory 34 to determine if the condition is normal. If the muscle is found to be in a normal condition, then normal operation continues. If the tests in step 112 determine that the muscle condition is abnormal, then in step 114 the muscle stimulation parameters are modified. For example, if the test in step 112 indicates that the muscle 16 is over-stimulated, then in step 114, the energy and/or the frequency of the stimulation pulses applied by stimulator 30 is decreased. Muscle stimulation is then continued using the new parameters. The abnormal condition of the muscle may be determined in step 112 to be temporary. For example, the muscle 16 may be tired. In this case, the stimulation parameters may be changed only for a preselected time period, or until, the condition of muscle 16 returns to normal. Thereafter, normal stimulation is resumed.

The data defining the condition of the muscle may be derived empirically from data collected from a population matching the patient. Alternatively, this data may be derived from the patient himself by putting the patient through a set of exercises, changing the stimulation pulses, and correlating various waveforms with the respective muscle conditions.

Instead of electrode 54, the EMG may be sensed through the stimulating electrodes or leads 23A, 23B. However, in this latter configuration, additional circuitry may be needed to eliminate or reduce post stimulation polarization artifacts. One such technique involves using two-, or even three-phase stimulation pulses.

Figure 3:
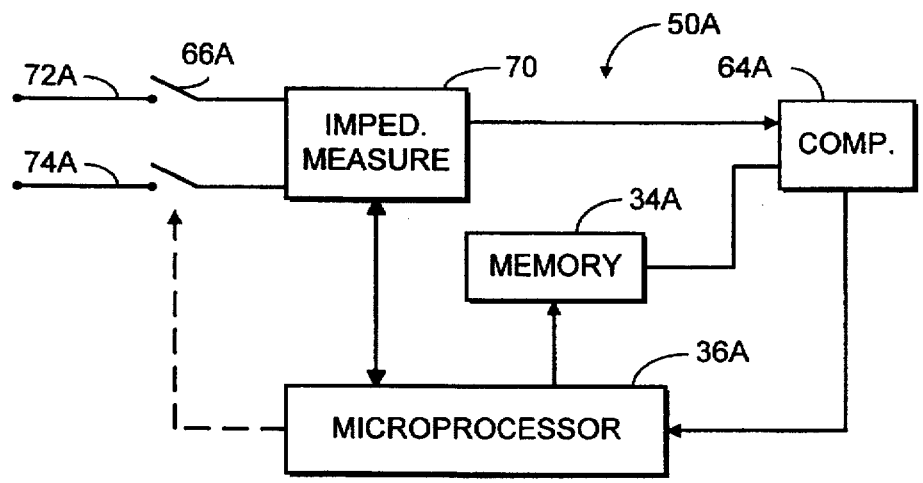
FIG. 3 shows a second muscle sensor for the cardiac device of FIG. 1.

Another embodiment of the invention is shown in FIG. 3. In this embodiment the muscle status sensor 50A consists of an impedance measurement circuit 70 for measuring an impedance between two input leads 72A, 74A. Leads 72A, 74A may be two intramuscular electrodes disposed either adjacent, between, or spaced apart from electrodes 18, 20, 54. Alternatively, the measurement may be made between any of the electrode leads and housing 13. Initially data is collected for impedance measurements corresponding to various conditions of the muscle and stored in memory 34A. Alternatively this information is derived from statistical data collected from other patients as discussed above. While the device 10 is in operation, impedance measurements are made at regular intervals by closing switch 66A. As in the previous embodiments, switch 66A is controlled by the micro-processor 36A. Each measurement is compared to data from memory 34 by comparator 64A and the result is used by the microprocessor 36A to determine the status of the muscle 16. Leads 72A, 74A could be unipolar or bipolar leads.

Figure 4:
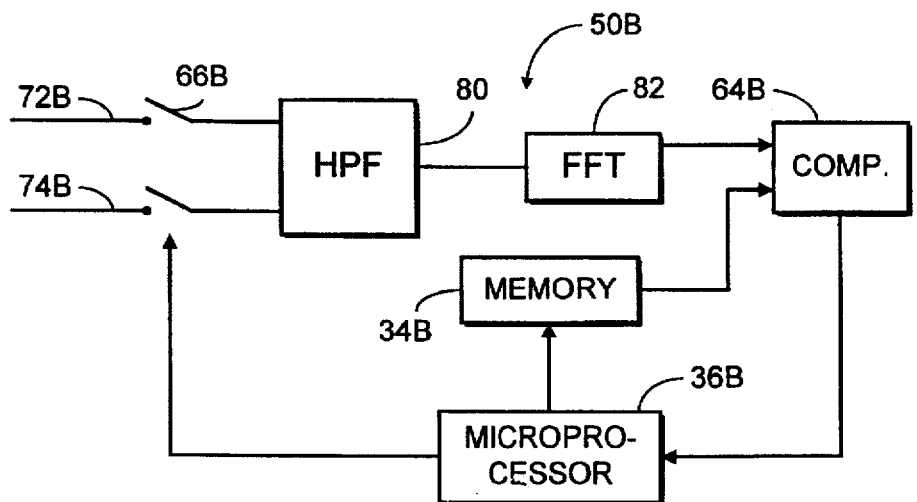
FIG. 4 shows a third muscle sensor for the cardiac device of FIG. 1.

Another embodiment of the invention is shown in FIG. 4. In this embodiment, the muscle sensor 50B includes a pair of input terminals 72B, 74B selectively connected to a high pass filter 80. The output of the filter 80 is fed to a fast Fourier transform analyzer 82. In this embodiment the high frequency content of the EMG signal is isolated by the filter 80 and analyzed by analyzer 82. The frequency response of a tired or un-trained muscle is different from the frequency response of a trained or well rested muscle. Accordingly, this response may be used as a criteria stored in memory 34B. During operation, the switch 66B is periodically closed by microprocessor 36B to make a measurement of the muscle status. The output of the analyzer 82 obtained for each measurement is compared by comparator 64B to the standards stored on memory 34B and this information is used by the microprocessor 36B to determine the muscle status.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

We claim:

1. An implantable cardiac apparatus for operating a muscle arranged to augment cardiac function, said apparatus comprising:

stimulation electrode means for delivering control pulses to said muscle to cause said muscle to selectively contract;

muscle monitoring means for determining a status of said muscle, said muscle monitoring means including a sensor for sensing an intrinsic electrical characteristic of said muscle and generating in response to said intrinsic electrical characteristic indicating signals; and pulse generator means for generating said control pulses in response to said indicating signals.

2. The apparatus of claim 1 wherein said intrinsic electrical characteristic is an electromyographic signal and wherein said muscle monitoring means monitors said electromyographic signal generated in said muscle.

3. The apparatus of claim 2 further comprising sensing electrode means for sensing said electromyographic signal, said sensing electrode means being separate from said stimulation electrode means.

4. The apparatus of claim 3 further comprising an implantable housing and wherein said sensing electrode means includes a sensing electrode, with said electromyographic signal being sensed between said sensing electrode and said housing.

5. The apparatus of claim 2 further comprising an implantable housing wherein said electromyographic signal is sensed between said stimulation electrode means and said housing.

6. The apparatus of claim 2 wherein said electromyographic signal is measured between a pair of stimulation electrodes.

7. The apparatus of claim 2 wherein said muscle monitoring means includes means for receiving said electromyographic signals, filtering means for filtering said electromyographic signal and rectifier means for rectifying the filter output.

8. The apparatus of claim 2 wherein said monitoring means includes high frequency means for sensing a high frequency component of said electromyographic signal.

9. The apparatus of claim 8 wherein said high frequency means includes a fast Fourier analyzer.

10. The apparatus of claim 1 further comprising sensing means for sensing a signal indicative of said muscle status and switching means for electrical disabling said sensing means.

11. The apparatus of claim 10 wherein said monitoring means includes an amplifier having inputs connected to said sensing means by said switching means, said inputs being connected to each other when not sensing muscle condition.

12. The apparatus of claim 11 wherein said switching means has a first position for coupling said inputs to said sensing means an a second position for grounding said inputs.

13. The apparatus of claim 1 wherein said intrinsic electrical characteristic is an impedance and said monitoring means includes an impedance measuring circuit for measuring said impedance.

14. A cardiac device for stimulating a muscle arranged and constructed to provide cardiac assistance, said device comprising:

a stimulation generator for generating muscle stimulation pulses in response to control signals;

sensing mean for sensing an intrinsic electrical characteristic of said muscle;

a monitoring means for determining a current condition of said muscle based on said intrinsic electrical characteristic to generate current muscle condition signals; and control means receiving said muscle condition signals, said control means generating said control signals, in accordance with said current muscle condition signals.

15. The device of claim 14 wherein said control means includes means for comparing said current muscle condition signals to a reference signal.

16. The device of claim 14 wherein said control means determines a current condition of said muscle and generates said control signals in accordance with said current condition.

17. A method for stimulating a muscle constructed and arranged to provide cardiac assistance to a patient, said method comprising the steps of:

applying muscle stimulation pulses to said muscle, said muscle stimulation pulses causing said muscle to contract;

sensing an intrinsic electrical characteristic of said muscle;

monitoring said intrinsic electrical characteristic to generate a current condition of said muscle; and modifying said muscle stimulation pulses, if necessary, in accordance with said current condition.

18. The method of claim 17 wherein said step of monitoring includes comparing said intrinsic electrical characteristic to a reference signal, said reference signal being related to an abnormal muscle condition.

19. The method of claim 18 wherein said step of sensing includes sensing an EMG signal in said muscle.

20. The method of claim 19 wherein said EMG signal is sensed between two electrodes extending into said muscle.

21. The method of claim 19 wherein said EMG signal is determined between an electrode extending into said muscle and a metallic casing.

22. The method of claim 18 wherein said step of sensing includes sensing an impedance.

23. The method of claim 18 wherein said step of sensing includes sensing a high frequency signal.

* * * * *